United States Patent
Uchiyama et al.

(10) Patent No.: US 11,598,680 B2
(45) Date of Patent: Mar. 7, 2023

(54) SYSTEM FOR ESTIMATING THERMAL COMFORT

(71) Applicant: DAIKIN INDUSTRIES, LTD., Osaka (JP)

(72) Inventors: Akira Uchiyama, Suita (JP); Teruo Higashino, Suita (JP); Hiroki Yoshikawa, Suita (JP)

(73) Assignee: Daikin Industries, Ltd., Osaka (JP)

(*) Notice: Subject to any disclaimer, the term of this patent is extended or adjusted under 35 U.S.C. 154(b) by 0 days.

(21) Appl. No.: 17/610,403

(22) PCT Filed: May 15, 2020

(86) PCT No.: PCT/JP2020/019515
§ 371 (c)(1),
(2) Date: Nov. 10, 2021

(87) PCT Pub. No.: WO2020/230895
PCT Pub. Date: Nov. 19, 2020

(65) Prior Publication Data
US 2022/0146335 A1 May 12, 2022

(30) Foreign Application Priority Data

May 15, 2019 (JP) .............................. JP2019-092087
Mar. 27, 2020 (JP) .............................. JP2020-057448

(51) Int. Cl.
*A61B 5/00* (2006.01)
*G01K 13/20* (2021.01)
(Continued)

(52) U.S. Cl.
CPC ................ *G01K 13/20* (2021.01); *A61B 5/01* (2013.01); *G01J 5/0025* (2013.01)

(58) Field of Classification Search
CPC .......... G01K 13/20; A61B 5/01; G01J 5/0025
(Continued)

(56) References Cited

U.S. PATENT DOCUMENTS

2004/0242976 A1* 12/2004 Abreu .................... A61B 5/746
600/315
2008/0146892 A1* 6/2008 LeBoeuf .................. A61B 5/02
600/300
(Continued)

FOREIGN PATENT DOCUMENTS

CN           203633541 U  *  6/2014
CN           104712573 A  *  6/2015
(Continued)

OTHER PUBLICATIONS

International Preliminary Report of corresponding PCT Application No. PCT/JP2020/019515 dated Nov. 25, 2021.
(Continued)

*Primary Examiner* — Gail Kaplan Verbitsky
(74) *Attorney, Agent, or Firm* — Global IP Counselors, LLP

(57) ABSTRACT

A system includes first and second acquisition units that acquire first and second biological information of a target, and an estimation unit. The first acquisition unit includes at least one first sensor. The second acquisition unit includes at least one second sensor different from the at least one first sensor. The estimation unit estimates a thermal comfort of the target based on the first and second biological information. The estimation unit further estimates a first thermal comfort of the target based on the first biological information, and the thermal comfort of the target based on the first and second biological information. When the second acquisition unit does not acquire the second biological information, the estimation unit sets, as the thermal comfort of the target, the first thermal comfort that is corrected using (Continued)

previous thermal comfort of the target estimated by the estimation unit based on at least the second biological information previously acquired by the second acquisition unit.

16 Claims, 7 Drawing Sheets

(51) Int. Cl.
*A61B 5/01* (2006.01)
*G01J 5/00* (2022.01)

(58) Field of Classification Search
USPC .......................................................... 374/109
See application file for complete search history.

(56) References Cited

U.S. PATENT DOCUMENTS

| | | | | |
|---|---|---|---|---|
| 2009/0216509 | A1* | 8/2009 | Baker | G06F 30/20 |
| | | | | 703/11 |
| 2009/0276062 | A1 | 11/2009 | Kanai et al. | |
| 2016/0018119 | A1* | 1/2016 | Desmet | F24F 11/0001 |
| | | | | 236/1 C |
| 2016/0136385 | A1* | 5/2016 | Scorcioni | A61B 5/4812 |
| | | | | 600/26 |
| 2016/0320081 | A1* | 11/2016 | Nikovski | F24F 11/30 |
| 2020/0333033 | A1 | 10/2020 | Kitagawa et al. | |
| 2021/0402258 | A1* | 12/2021 | Washington | A63B 22/02 |

FOREIGN PATENT DOCUMENTS

| | | | | | |
|---|---|---|---|---|---|
| CN | 105997400 | A | * | 10/2016 | |
| CN | 104235997 | B | * | 3/2017 | |
| CN | 104998332 | B | * | 6/2018 | |
| CN | 109278490 | A | * | 1/2019 | |
| CN | 109489202 | A | * | 3/2019 | ............. F24F 11/64 |
| CN | 112631135 | A | * | 4/2021 | ........... G01J 5/0025 |
| DE | 102004011139 | A1 | * | 10/2005 | ........... A41D 13/002 |
| DE | 102016201908 | A1 | * | 8/2017 | ............. A61B 5/055 |
| JP | H09137989 | A | * | 5/1997 | |
| JP | WO2007/007632 | A1 | | 1/2007 | |
| JP | 2011102683 | A | * | 5/2011 | |
| JP | 2012-154591 | A | | 8/2012 | |
| JP | WO2015/122201 | A1 | | 8/2015 | |
| JP | 2016-182504 | A | | 10/2016 | |
| JP | 2017-62060 | A | | 3/2017 | |
| JP | 2018-185108 | A | | 11/2018 | |
| JP | 2019-17946 | A | | 2/2019 | |
| JP | 2022022563 | A | * | 2/2022 | |
| WO | WO2014071046 | A1 | * | 5/2014 | |
| WO | WO-2017213011 | A1 | * | 12/2017 | ............... A61B 5/01 |
| WO | WO-2018214001 | A1 | * | 11/2018 | ............... F24F 11/62 |
| WO | WO-2019078308 | A1 | * | 4/2019 | ........... A42B 3/0433 |
| WO | 2019/87537 | A1 | | 5/2019 | |
| WO | WO-2021049573 | A1 | * | 3/2021 | |
| WO | WO-2021086684 | A1 | * | 5/2021 | ............. F24F 11/30 |

OTHER PUBLICATIONS

International Search Report of corresponding PCT Application No. PCT/JP2020/019515 dated Jul. 14, 2020.
Hiroki Yoshikawa et al., "Thermal Comfort Estimation by Sensor Fusion to Reduce Spatial Energy Consumption", 4th vol. of lecture proceedings of 19th Forum on Information Technology 2019, pp. 71-74, Aug. 20, 2019.

\* cited by examiner (a) RANDOM FOREST (b) KNN (c) SVM

SYSTEM FOR ESTIMATING THERMAL COMFORT

CROSS-REFERENCE TO RELATED APPLICATIONS

This U.S. National stage application claims priority under 35 U.S.C. § 119(a) to Japanese Patent Application Nos. 2019-092087, filed in Japan on May 15, 2019 and 2020-057448, filed in Japan on Mar. 27, 2020, the entire contents of which are hereby incorporated herein by reference.

BACKGROUND

Field of the Invention

The present disclosure relates to a system for estimating thermal comfort.

Background Information

As described in Japanese Unexamined Patent Application Publication No. 2019-017946, a system is available that estimates information on a subject using sensors disposed in a wearable sensor to acquire information such as a heart rate, a skin temperature, and a skin potential.

SUMMARY

Biological information such as a heart rate, which is acquired using an apparatus such as a wearable sensor, has a large error, and information estimated based on the biological information may have low accuracy.

A system according to a first aspect includes a first acquisition unit, a second acquisition unit, and an estimation unit. The first acquisition unit acquires first biological information of a target. The first acquisition unit is constituted by one or more sensors. The second acquisition unit acquires second biological information of the target. The second acquisition unit is constituted by one or more sensors different from the one or more sensors of the first acquisition unit. The estimation unit estimates a first thermal comfort of the target on the basis of the first biological information. The estimation unit estimates a thermal comfort of the target on the basis of the first biological information and the second biological information. When the second acquisition unit does not acquire the second biological information, the estimation unit sets, as the thermal comfort of the target, the first thermal comfort that is corrected on the basis of the second biological information previously acquired by the second acquisition unit.

Accordingly, the system according to the present disclosure can acquire a more accurate thermal comfort of the target.

A system according to a second aspect includes a first acquisition unit, a second acquisition unit, a first estimation unit, a second estimation unit, and a correction unit. The first acquisition unit acquires first biological information of a target. The first acquisition unit is constituted by one or more sensors. The second acquisition unit acquires second biological information of the target. The second acquisition unit is constituted by one or more sensors different from the one or more sensors of the first acquisition unit. The first estimation unit estimates a first thermal comfort of the target on the basis of the first biological information acquired by the first acquisition unit. The second estimation unit estimates a thermal comfort of the target on the basis of the first biological information and the second biological information. The correction unit corrects the first thermal comfort, when the second acquisition unit does not acquire the second biological information, on the basis of the second biological information previously acquired by the second acquisition unit.

A system according to a third aspect includes a first acquisition unit, a second acquisition unit, a first estimation unit, a second estimation unit, and a correction unit. The first acquisition unit acquires first biological information of a target. The first acquisition unit is constituted by one or more sensors. The second acquisition unit acquires second biological information of the target. The second acquisition unit is constituted by one or more sensors different from the one or more sensors of the first acquisition unit. The first estimation unit estimates a first thermal comfort of the target on the basis of the first biological information acquired by the first acquisition unit. The second estimation unit estimates a second thermal comfort of the target on the basis of the first biological information acquired by the first acquisition unit and the second biological information acquired by the second acquisition unit. The system causes the first estimation unit to learn using the first biological information acquired by the first acquisition unit and an estimation result estimated by the second estimation unit as a teacher data set. When the first estimation unit performs estimation, the system outputs the first thermal comfort on the basis of the first biological information acquired by the first acquisition unit.

A system according to a fourth aspect is the system according to any of the first aspect to the third aspect, in which the first acquisition unit acquires the first biological information while being in contact with the living body. The second acquisition unit acquires the second biological information without coming into contact with the living body.

A system according to a fifth aspect is the system according to any of the first aspect to the fourth aspect, in which the first acquisition unit acquires, as the first biological information, at least information on any one of a heart rate, a body surface temperature, or an electrodermal activity (EDA: Electro-Dermal Activity) of the target.

A system according to a sixth aspect is the system according to any of the first aspect to the fifth aspect, in which the second acquisition unit acquires, as the second biological information, at least information on a body surface temperature of a face of the target and information on a body surface temperature of a part of the face.

A system according to a seventh aspect is the system according to any of the first aspect to the sixth aspect, in which the number of types of information included in the second biological information is larger than the number of types of information included in the first biological information.

A system according to an eighth aspect is the system according to any of the first aspect to the seventh aspect, in which the second thermal comfort has higher accuracy than the first thermal comfort.

A system according to a ninth aspect is the system according to any of the first aspect to the eighth aspect, in which the number of sensors included in the second acquisition unit is larger than the number of sensors included in the first acquisition unit.

A system according to a tenth aspect is the system according to any of the first aspect to the ninth aspect, further including a second determination unit. The second determination unit determines whether the second biological information acquired by the second acquisition unit is effective information. The second estimation unit estimates the second thermal comfort in a case where the second determination unit determines that the second biological information is effective.

A system according to an eleventh aspect is the system according to any of the first aspect to the tenth aspect, further including a first determination unit. The first determination unit determines whether the first biological information acquired by the first acquisition unit is effective information. The first estimation unit estimates the first thermal comfort in a case where the first determination unit determines that the first biological information is effective.

A system according to a twelfth aspect is the system according to any of the first aspect to the eleventh aspect, in which the first estimation unit further estimates the first thermal comfort on the basis of the first biological information previously acquired by the first acquisition unit. Alternatively, the second estimation unit further estimates the second thermal comfort on the basis of the second biological information previously acquired by the second acquisition unit.

A system according to a thirteenth aspect is the system according to any of the first aspect to the twelfth aspect, further including a third acquisition unit that acquires information on a thermal environment surrounding the target.

A system according to a fourteenth aspect is the system according to the thirteenth aspect, in which the third acquisition unit acquires information on an ambient temperature and/or an ambient humidity of the living body.

A system according to a fifteenth aspect is the system according to the first aspect, in which the estimation unit learns using the first biological information, the second biological information, and the thermal comfort as teacher data. The estimation unit estimates the thermal comfort on the basis of the first biological information and the second biological information. The estimation unit stores the estimated thermal comfort of the target. The estimation unit has a function of outputting dummy information when the second acquisition unit does not acquire the second biological information. The estimation unit learns using the first biological information, the dummy information, and the thermal comfort as teacher data. The estimation unit sets, as the thermal comfort of the target, the first thermal comfort that is corrected on the basis of the first biological information, the dummy information, and the stored thermal comfort.

A system according to a sixteenth aspect is the system according to the first aspect, in which the estimation unit learns using the first biological information, the second biological information, and the thermal comfort as teacher data. The estimation unit estimates the thermal comfort on the basis of the first biological information and the second biological information. The estimation unit stores the estimated thermal comfort of the target. The estimation unit has a function of outputting dummy information when the second acquisition unit does not acquire the second biological information. The estimation unit learns using the first biological information, the dummy information, and the thermal comfort as teacher data. The estimation unit learns using the first biological information, the dummy information, and the stored thermal comfort as teacher data, and sets, as the thermal comfort of the target, the first thermal comfort that is estimated on the basis of the first biological information and the dummy information.

DETAILED DESCRIPTION OF EMBODIMENT(S)

An embodiment of the present disclosure will be described hereinafter. It should be noted that the following embodiments are specific examples and are not intended to limit the technical scope, but can be modified, as appropriate, without departing from the spirit of the disclosure.

(1) First Embodiment (1-1) Overview

Figure 1:
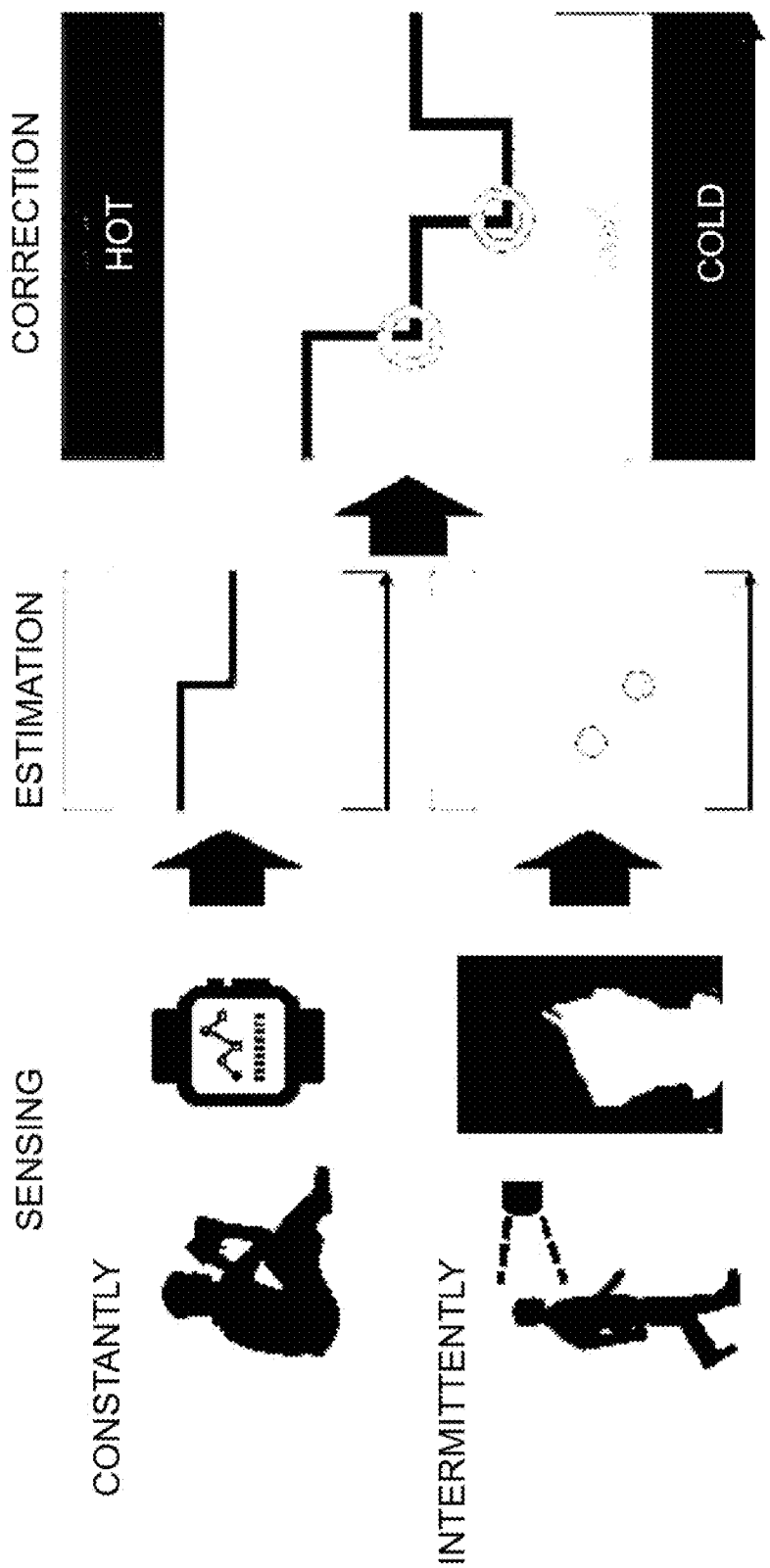
FIG. 1 is a schematic diagram of a system.

FIG. 1 is a schematic diagram of a system presented in the present disclosure. As illustrated in FIG. 1, in the system presented in the present disclosure, an estimated value having a relatively large error, which is obtained using an arm sensor 10 capable of constant sensing, is corrected by an accurate estimated value based on thermal images that can be intermittently acquired. A thermal image is acquired by using a thermography or the like included in an air conditioning apparatus 20. A random forest is used as an estimation algorithm, and two types of estimation models are selectively used in accordance with each piece of sensor data to be obtained. The feature quantities that are used are shown in Table 1.

TABLE 1

| # | Feature name | quantity | Description |
|---|---|---|---|
| $f_1$ | $T_{face}$ | | Average body surface temperature of the entire face |
| $f_2$ | $T_{forehead}$ | | Body surface temperature of the forehead |
| $f_3$ | $T_{cheek\_r}$ | | Body surface temperature of the right cheek |
| $f_4$ | $T_{cheek\_1}$ | | Body surface temperature of the left cheek |
| $f_5$ | $T_{nose}$ | | Body surface temperature of the tip of the nose |
| $f_6$ | $T_{mouth}$ | | Body surface temperature around the mouth |
| $f_7$ | $T_{max}$ | | Maximum value of the body surface temperature of the face |
| $f_8$ | $T_{min}$ | | Minimum value of the body surface temperature of the face |
| $f_9$ | $T_{var}$ | | Variance of the body surface temperature of the face |
| $f_{10}$ | WT | | Body surface temperature of the wrist |
| $f_{11}$ | $WT_{mean\_1min}$ | | Average value of the body surface temperature of the wrist in the past 1 minute |
| $f_{12}$ | $WT_{mean\_5min}$ | | Average value of the body surface temperature of the wrist in the past 5 minutes |

TABLE 1-continued

| # | Feature name | quantity | Description |
|---|---|---|---|
| $f_{13}$ | $WT_{mean\_10min}$ | | Average value of the body surface temperature of the wrist in the past 10 minutes |
| $f_{14}$ | $WT_{diff\_1min}$ | | Difference between the value obtained 1 minute before and the current value of the body surface temperature of the wrist |
| $f_{15}$ | $WT_{diff\_5min}$ | | Difference between the value obtained 5 minutes before and the current value of the body surface temperature of the wrist |
| $f_{16}$ | $WT_{diff\_10min}$ | | Difference between the value obtained 10 minutes before and the current value of the body surface temperature of the wrist |
| $f_{17}$ | HR | | Heart rate |
| $f_{18}$ | $HR_{mean\_1min}$ | | Average value of the heart rate in the past 1 minute |
| $f_{19}$ | $HR_{mean\_5min}$ | | Average value of the heart rate in the past 5 minutes |
| $f_{20}$ | $HR_{mean\_10min}$ | | Average value of the heart rate in the past 10 minutes |
| $f_{21}$ | $HR_{diff\_1min}$ | | Difference between the value obtained 1 minute before and the current value of the heart rate |
| $f_{22}$ | $HR_{diff\_5min}$ | | Difference between the value obtained 5 minutes before and the current value of the heart rate |
| $f_{23}$ | $HR_{diff\_10min}$ | | Difference between the value obtained 10 minutes before and the current value of the heart rate |
| $f_{24}$ | EDA | | Skin potential |
| $f_{25}$ | $EDA_{mean\_1min}$ | | Average value of the skin potential in the past 1 minute |
| $f_{26}$ | $EDA_{mean\_5min}$ | | Average value of the skin potential in the past 5 minutes |
| $f_{27}$ | $EDA_{mean\_10min}$ | | Average value of the skin potential in the past 10 minutes |
| $f_{28}$ | $EDA_{diff\_1min}$ | | Difference between the value obtained 1 minute before and the current value of the skin potential |
| $f_{29}$ | $EDA_{diff\_5min}$ | | Difference between the value obtained 5 minutes before and the current value of the skin potential |
| $f_{30}$ | $EDA_{diff\_10min}$ | | Difference between the value obtained 10 minutes before and the current value of the skin potential |
| $f_{31}$ | HC | | State of use of the cooling or heating operation (cooling: −1, heating: 1) |

When a thermal image is obtained from the air conditioning apparatus 20, all of f1 to f31 are given as feature quantities to perform accurate estimation, whereas, normally, estimation is performed only from f10 to f30, which are obtained from the arm sensor 10, and the state of use of the cooling or heating operation (f31).

(1-2) Extraction of Face Temperature Feature Quantities

Extraction of a temperature from the thermal image acquired from the air conditioning apparatus 20 is performed by, for example, a combination of a visible image and the thermal image. First, in the visible image, the coordinates of a face as a rectangle are acquired using a face detection method. The present disclosure uses a face detector that utilizes Haar-liKe feature in OPenCV. The rectangular coordinates of parts of the face (faCe, forehead, CheeK-r, CheeK-1, nose, and mouth) are relatively calculated from the obtained rectangle. Calculation formulas are shown in Table 2.

TABLE 2

| Part | x coordinate, | y coordinate | Horizontal width, | Vertical width |
|---|---|---|---|---|
| Forehead (forehead) | X −W/16, | Y −H/4 | W/8, | H/8 |
| Right cheek (cheek_r) | X −3W/10, | Y +H/16 | W/6, | H/4 |
| Left cheek (cheek_l) | X +2W/15, | Y +H/16 | W/6, | H/4 |
| Nose (nose) | X −W/16, | Y | W/8, | H/8 |
| Mouth (mouth) | X −W/8, | Y +H/4 | W/4, | H/8 |

X, Y, W, and H denote the center x coordinate, the center y coordinate, the horizontal width, and the vertical width of the detected face rectangle (face), respectively.

The rectangular coordinates of each part are calculated using the center coordinates (X; Y) and the lengths of the horizontal and vertical sides (W; H) of the face acquired by face detection. The temperatures of the parts (TfaCe; Tforehead; TCheeK-r; TCheeK-l; Tnose; Tmouth) are obtained by calculating the average temperatures thereof in the rectangle according to Equation (1).

< Math. 1 >

$$T_P = \frac{\sum_{(x,y) \in P} T(x, y)}{|P|} \quad (1)$$

Here, P represents a set of coordinates of each part in the rectangle. T(x; y) denotes the temperature acquired from the coordinates in the thermal image corresponding to the coordinates (x; y) in the visible image, and |P| denotes the number of coordinate points included in the set P. Tmax, Tmin, and Tvar are calculated according to Equation (2), Equation (3), and Equation (4), respectively. Here, max(X) represents the maximum value of the set X, and min(X) represents the minimum value of the set X.

< Math. 2 >

$$T_{max} = \max(T(x, y)) \quad (2)$$

< Math. 3 >

$$T_{min} = \min(T(x, y)) \quad (3)$$

< Math. 4 >

$$T_{var} = \frac{\sum_{(x,y) \in P} (T(x, y))^2}{|P|} - T_P^2 \quad (4)$$

(1-3) Extraction of Arm Sensor Feature Quantities

The arm sensor 10 includes a plurality of sensors and acquires a body surface temperature of a wrist (WT), a heart rate (HR), and a skin potential (EDA). These sensors are mounted in many arm sensors and are also closely related to the thermal comfort level. The body surface temperature (WT), the heart rate (HR), and the skin potential (EDA) at the point in time when estimation is performed are used as feature quantities. Since the temporal change is also related to the thermal comfort level, the average values of each of the feature quantities described above in the past 1 minute, 5 minutes, and 10 minutes and the differences from the values of each of the feature quantities described above obtained 1 minute before, 5 minutes before, and 10 minutes before are also used as feature quantities. The respective calculation formulas are given by Equation (5) and Equation (6).

<Math. 5>

$$X_{mean\_nmin}(t_c) = \frac{\sum_{t=0}^{60n}(X(t_c - t))}{60n} \quad (5)$$

<Math. 6>

$$X_{diff\_nmin}(t_c) = X(t_c) - X(t_c - 60n) \quad (6)$$

Here, X represents any of the body surface temperature (WT), the heart rate (HR), or the skin potential (EDA), n represents any of 1, 5, or 10, X(t) represents a value measured by each sensor at time t, and tC represents the current time. In the present disclosure, an average value for each piece of sensor data is calculated every second to reform a data sequence g of 1 (Hz).

(1-4) State of Use of Cooling or Heating Operation

The air conditioning apparatus 20 can acquire the state of use of the cooling or heating operation of the air conditioning apparatus 20 via a sensor or the like. Alternatively, the air conditioning apparatus 20 can acquire the state of use of the cooling or heating operation of another air conditioning apparatus via wired or wireless communication. The state of use of the cooling or heating operation is an important feature quantity for estimating the thermal comfort level, and, as the feature quantity, −1 is given during cooling whereas 1 is given during heating. In the present disclosure, after the thermal comfort level is estimated, whether there is room for energy reduction is determined from the state of use of the cooling or heating operation and the thermal comfort level at that point in time. Specifically, a state in which the user feels cool (the thermal comfort level has a negative value) during cooling (HC=−1) and a state in which the user feels warm (the thermal comfort level has a positive value) during heating (HC=1) are defined as a state in which extra energy is used. Detecting such a state can reduce energy used for cooling and heating.

(1-5) Correction Based on Previous Estimation Result

In the present disclosure, the estimation model is switched between a state in which sensor data is acquired only from the arm sensor 10 and a state in which a thermal image is acquired from the air conditioning apparatus 20 to estimate the thermal comfort level. In the present disclosure, the time window is 1 minute, and an estimated value based on the preceding thermal image and an estimated value obtained by the arm sensor 10 at the current time are combined to calculate a corrected estimated value. This value is used as the thermal comfort level at the current time. Correction formulas are given by Equation (7) and Equation (8).

<Math. 7>

$$C_{est}(t) = a^{t_e} C_{prev} + (1 - a^{t_e}) C_{wrist}(t) \quad (7)$$

<Math. 8>

$$t_e = t - t_{prev} \quad (8)$$

Here, CPrev denotes an accurate estimated value at the point in time at which the preceding thermal image was acquired, and tPrev denotes the time at which the preceding thermal image was acquired. Cwrist(t) denotes an estimated value obtained by the arm sensor 10 at time t. A weight a (0<a<1) is set to 0.9 in the present disclosure. As a result, an elapsed time to from the acquisition of the thermal image is used to take into account a reduction in the reliability of estimation based on the thermal image over time.

(1-6) Experimental Environment

Figure 2:
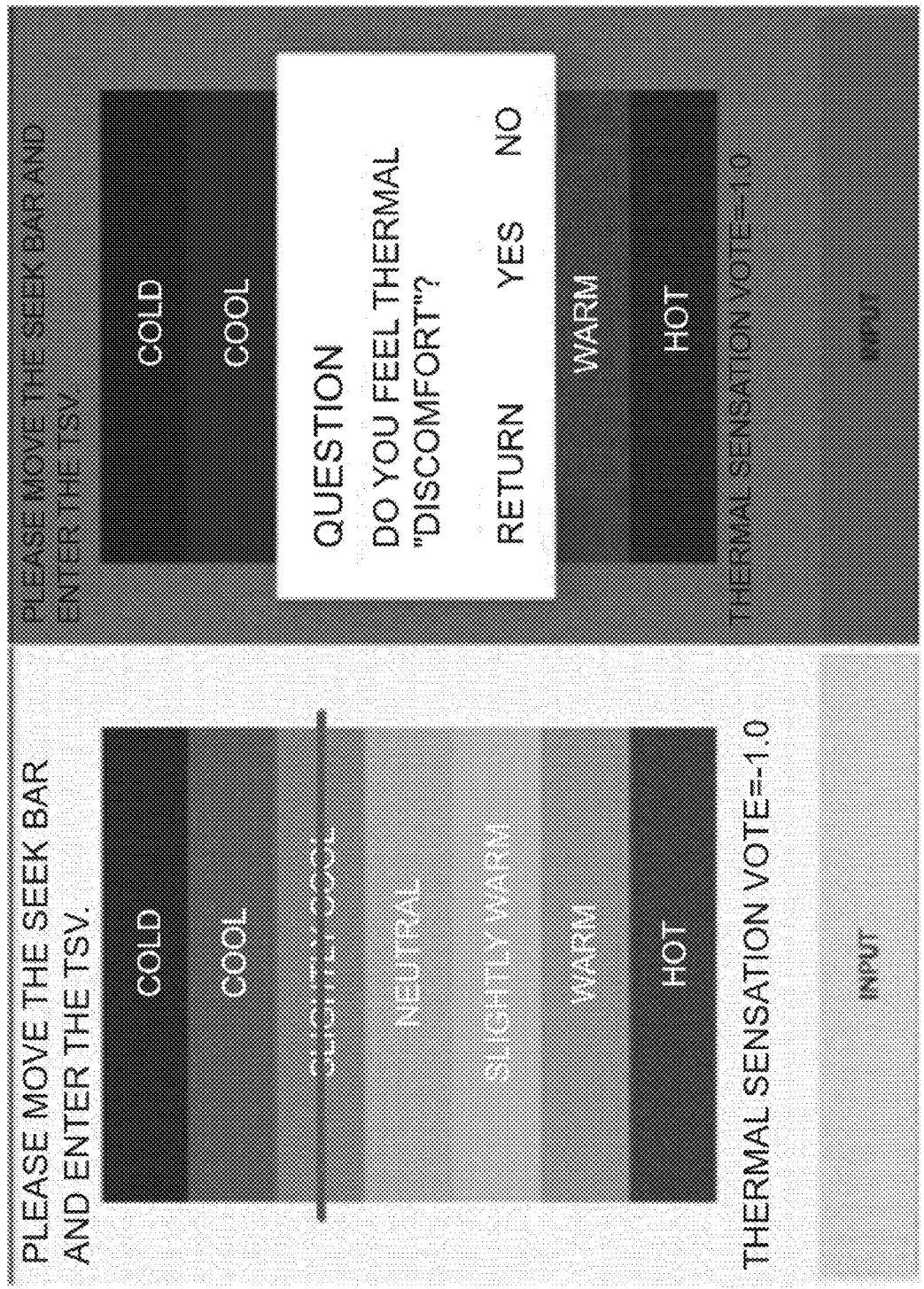
FIG. 2 illustrates an example of a smartphone application.

In the present disclosure, to construct a thermal comfort level estimation model supporting the cooling and heating operations, an experiment was performed for each season, and data for a total of 128 days was collected from 15 male test subjects in their 20s. During the experiment, each of the test subjects performed daily research activities while constantly wearing the arm sensor 10, a visible image and a thermal image thereof were captured seven times at intervals of 10 seconds every 30 minutes, and, at the same time, they reported which of the seven thermal comfort level labels they are in by using a smartphone application illustrated in FIG. 2. In addition, at the same time, a survey asking whether they feel comfortable or uncomfortable was taken to investigate the relationship between the seven thermal comfort levels and the thermal discomfort of users. In this experiment, 10724 visible images and 10724 thermal images were acquired. Further, the average value of temperature information was calculated from a set of seven thermal images at each point in time and used as temperature information at that point in time. As a result, a set of thermal images acquired at 1476 points, data of the arm sensor 10, and the thermal comfort level after a loss of sensor data has been eliminated is used as a data set. The details of the reported values of the thermal comfort levels are shown in Table 3.

TABLE 3

| Thermal comfort level | Number of reports | Number of discomfort labels |
|---|---|---|
| −3 (cold) | 11 | 11 |
| −2 (cool) | 43 | 0 |
| −1 (slightly cool) | 185 | 0 |
| 0 (neutral) | 919 | 0 |
| 1 (slightly warm) | 257 | 0 |
| 2 (warm) | 55 | 0 |
| 3 (hot) | 6 | 6 |

Here, discomfort labels were reported only for the extreme thermal environments (−3 and 3).

(1-7) Estimation Using Thermal Image

All of the feature quantities in Table 1 are used for estimation using a thermal image. KNN (K-nearest neighbor algorithm), SVM (support vector machine), and a method for estimating all as 0 (neutral), are used as comparative methods. The estimation accuracies of the respective methods, which were calculated by five-fold cross-validation, are shown in Table 4.

TABLE 4

| Estimation method | Accuracy (correct answer rate) | Mean absolute error |
| --- | --- | --- |
| Random forest | 65.5% | 0.40 |
| KNN | 55.7% | 0.54 |
| SVM | 64.6% | 0.41 |
| Neutral | 62.2% | 0.47 |

Figure 3:
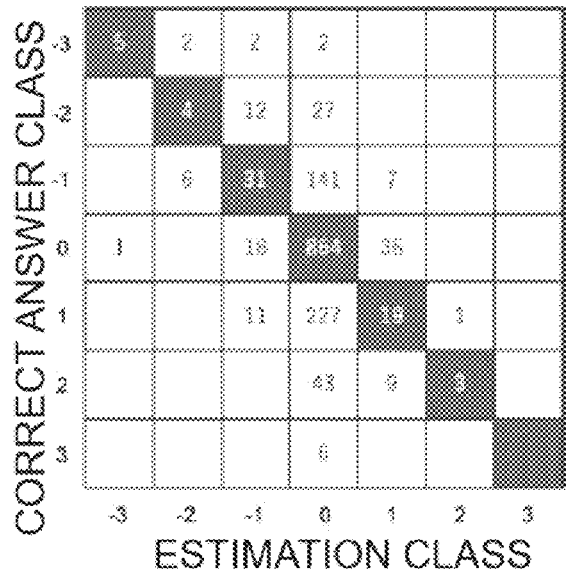
FIG. 3 illustrates confusion matrices for estimation using thermal images.
Figure 3:
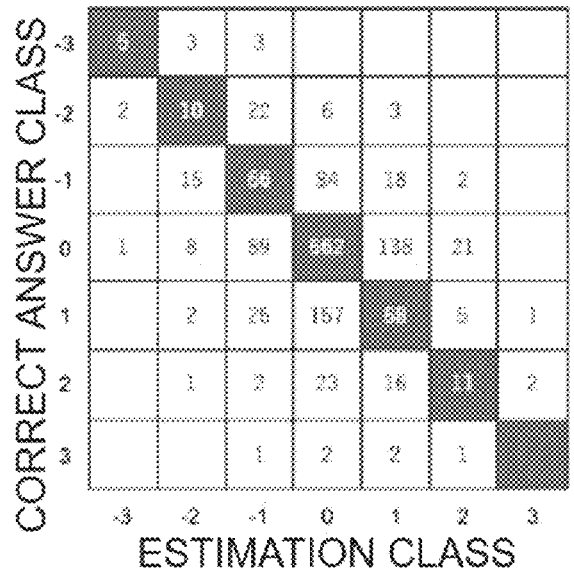
Figure 3:
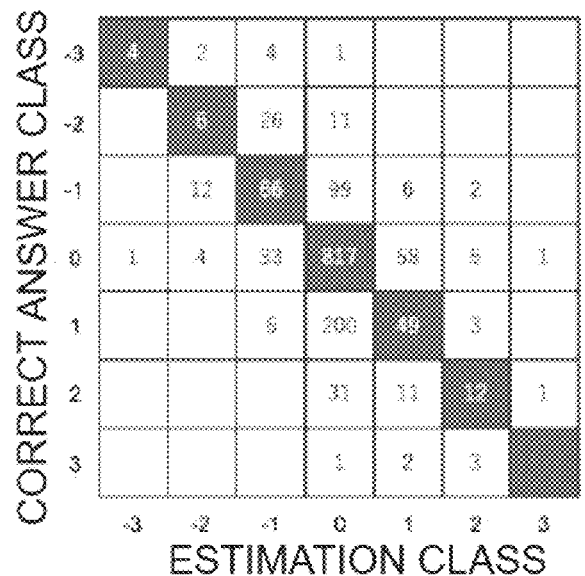

The random forest resulted in having the highest accuracy for both the estimation accuracy and the mean absolute error based on seven-class classification. FIG. 3 illustrates confusion matrices of the random forest, KNN, and SVM. According to this, in the random forest, the respective classes (−3, −2, −1, 0, 1, 2, 3) have recall rates of 54.5%, 23.3%, 27.6%, 94.0%, 12.8%, 5.4%, and 0%, and precision rates of 85.7%, 45.5%, 53.1%, 68.3%, 39.8%, 75.0%, and none. This indicates that it is difficult to perform estimation of −2, −1, and 1. In contrast, in the estimation based on the random forest, the probability of erroneously estimating that the user feels warm (1, 2, 3) when the user feels cool (−3, −2, −1) is 2.9%, and the probability of estimating that the user feels cool when the user feels warm is 3.4%, which are almost none. The results indicate that extra energy consumption in the cooling and heating operations is sensed and there is substantially no erroneous detection in suppressing the air conditioning output. From the reasons described above, it is found that the present method is very effective as a method for reducing energy consumption without impairing the thermal comfort level.

(1-8) Estimation Only Using Arm Sensor

Estimation only using the arm sensor 10 uses f10 to f31 in Table 1. The estimation accuracies of the respective methods, which were calculated by five-fold cross-validation, are shown in Table 5.

TABLE 5

| Estimation method | Accuracy (correct answer rate) | Mean absolute error |
| --- | --- | --- |
| Random forest | 62.7% | 0.44 |
| KNN | 49.0% | 0.64 |
| SVM | 62.6% | 0.46 |
| Neutral | 62.2% | 0.47 |

Figure 4:
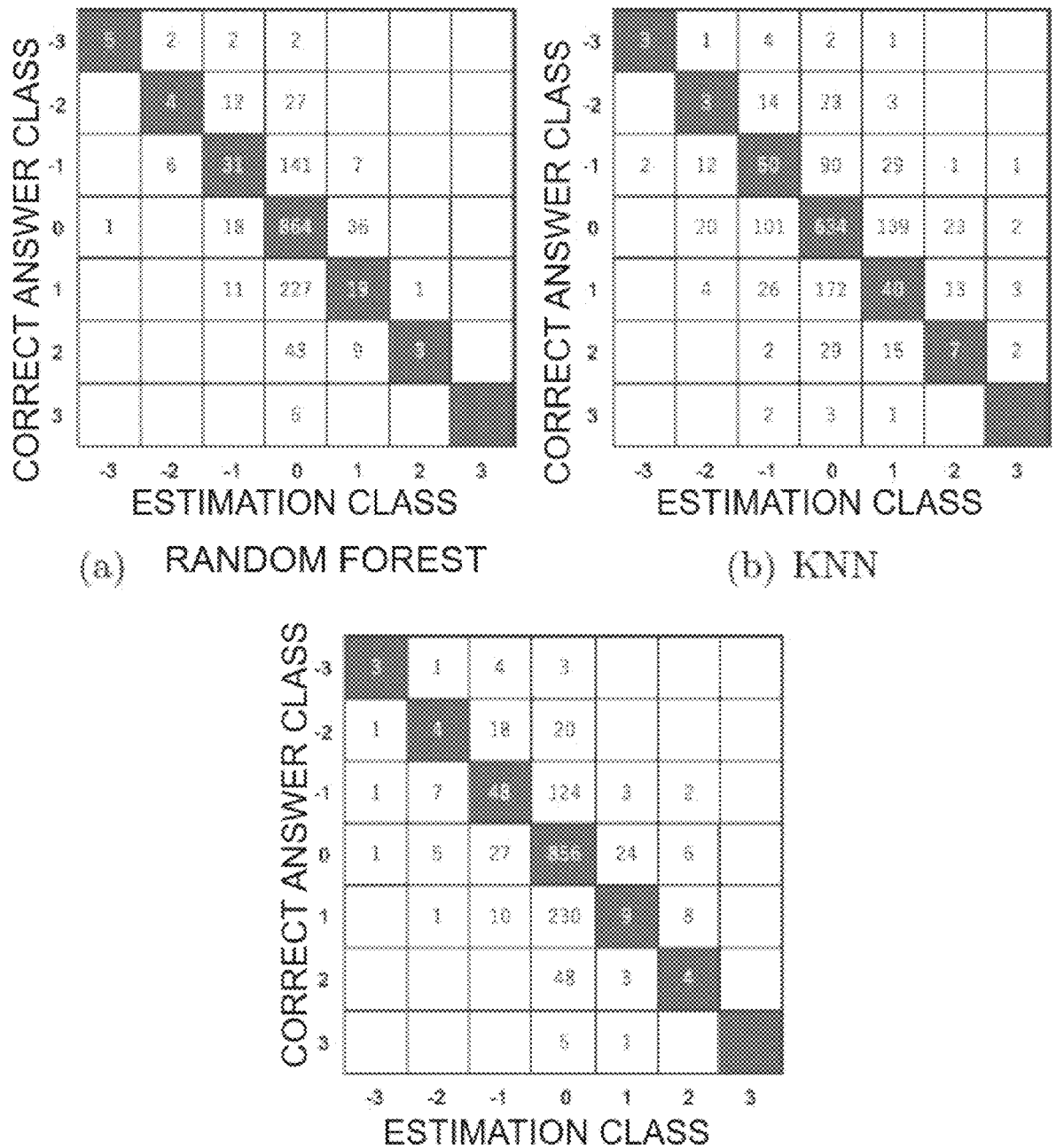
FIG. 4 illustrates confusion matrices for estimation using an arm sensor.

The random forest resulted in having the highest accuracy for both the estimation accuracy and the mean absolute error based on seven-class classification. FIG. 4 illustrates confusion matrices of the respective methods. These results have similar tendencies to those in FIG. 3, which can be said to be effective for the sensing of extra energy consumption, and the accuracies remain slightly low because the numbers of dimensions of the feature quantities are small. Therefore, to achieve more accurate estimation, it is necessary to perform intermittent correction using thermal images.

(1-9) Sensing of Extra Energy Consumption

Figure 5A:
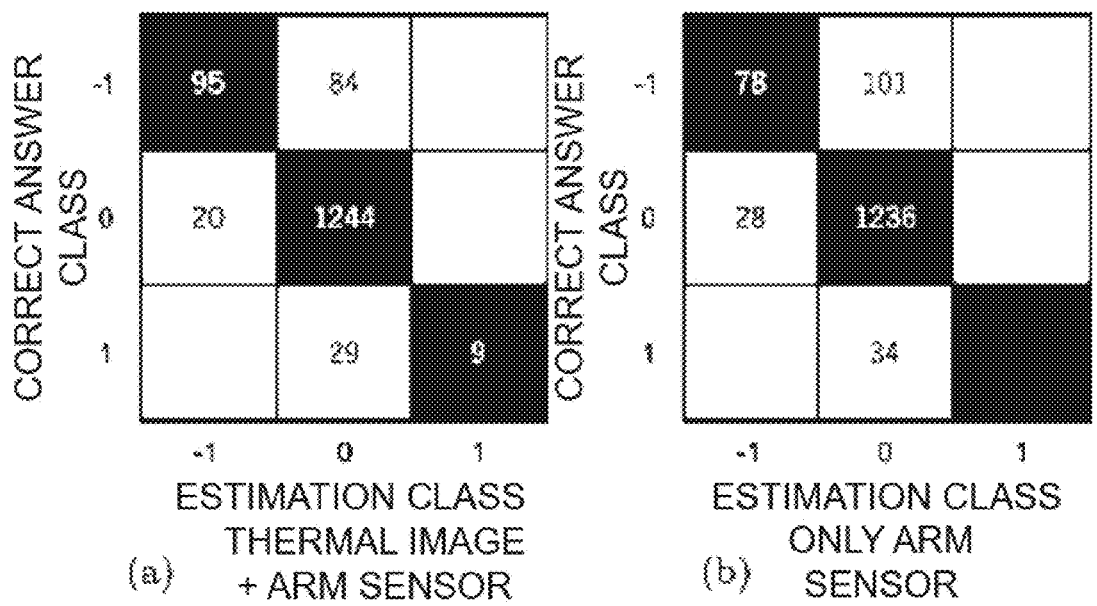
FIG. 5A includes confusion matrices indicating the state of energy consumption.
Figure 5B:
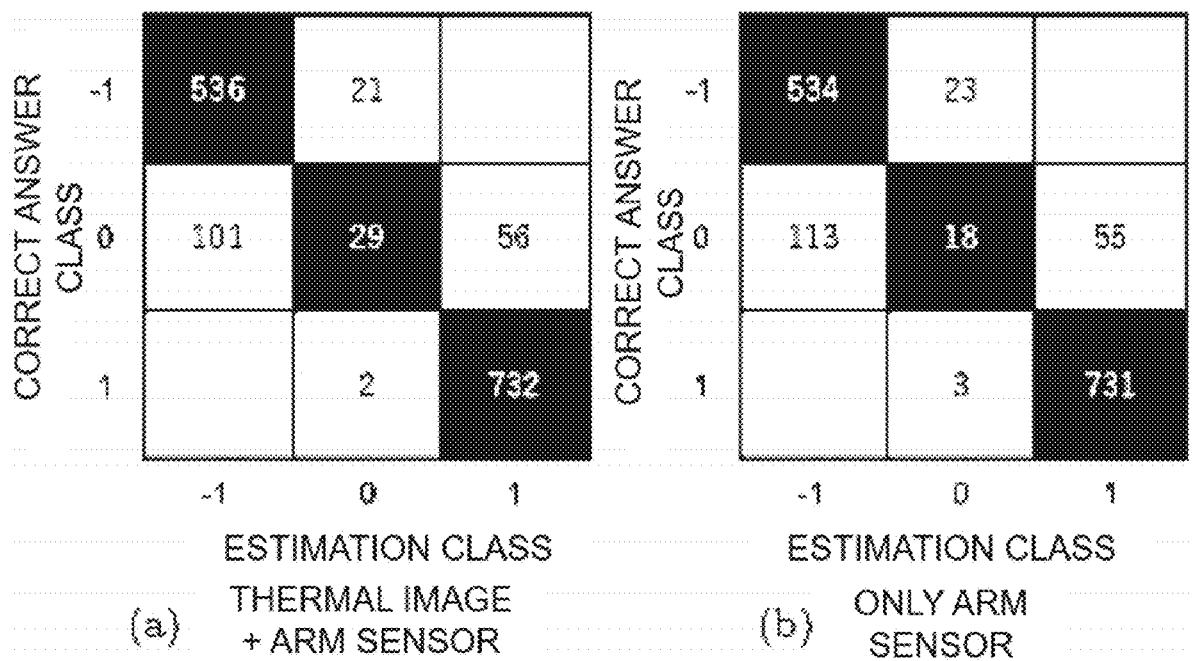
FIG. 5B includes confusion matrices indicating the state of energy consumption.

It is an object of the present disclosure to estimate the thermal comfort level of a user to sense extra energy consumption during cooling and heating, thereby reducing energy consumption. The state of extra energy consumption is set as an excess energy consumption state, and confusion matrices of results obtained by estimation using the random forest in a case where the excess energy consumption state is defined by (thermal comfort level)*HC>0 (−3, −2, −1 for cooling; 3, 2, 1 for heating) and in a case where the excess energy consumption state is defined by (thermal comfort level)*HC⊇0 (−3, −2, −1, 0 for cooling; 3, 2, 1, 0 for heating) are illustrated in FIG. 5A and FIG. 5B, respectively. In FIG. 5A, a state in which the thermal comfort level is less than 0 during cooling is defined as −1, a state in which the thermal comfort level is larger than 0 during heating is defined as 1, and other states are defined as 0, indicating a state in which there is no room for energy consumption reduction. In FIG. 5B, a state in which the thermal comfort level is less than or equal to 0 during cooling is defined as −1, a state in which the thermal comfort level is greater than or equal to 0 during heating is defined as 1, and other states are defined as 0, indicating a state in which there is no room for energy consumption reduction. On the basis of the definitions described above, three-class classification was performed. The results in FIG. 5A indicate that, in the estimation of the excess energy consumption state in which classes −1 and 1 are added together, when the thermal image and the arm sensor 10 are used in combination, sensing can be performed with a precision rate of 83.9% and a recall rate of 47.9%, and when only the arm sensor 10 is used, sensing can be performed with a precision rate of 73.6% and a recall rate of 36.6%. The results in FIG. 5B indicate that, in the estimation of the excess energy consumption state, when the thermal image and the arm sensor 10 are used in combination, sensing can be performed with a recall rate of 98.2% and a precision rate of 89.0%, and when only the arm sensor 10 is used, sensing can be performed with a recall rate of 98.0% and a precision rate of 88.3%. While it is desirable to select these models in accordance with the user's preference, it has been found that the excess energy consumption state can be accurately estimated without causing the user to feel thermal discomfort.

(1-10) Evaluation of Corrected Estimated Value

Figure 6A:
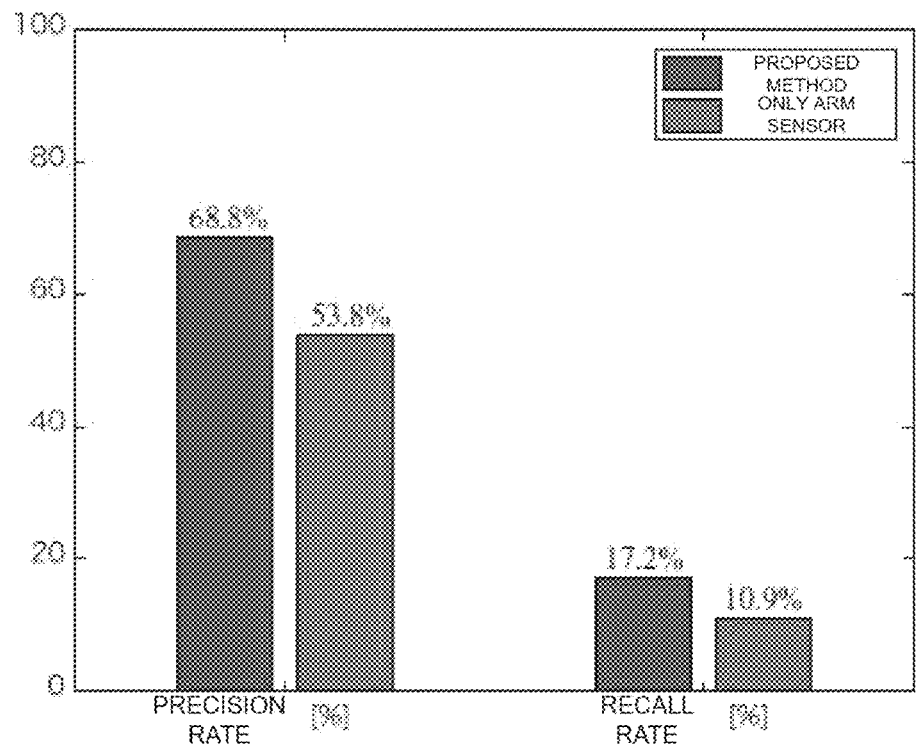
FIG. 6A is a diagram illustrating evaluation of a corrected estimated value.
Figure 6B:
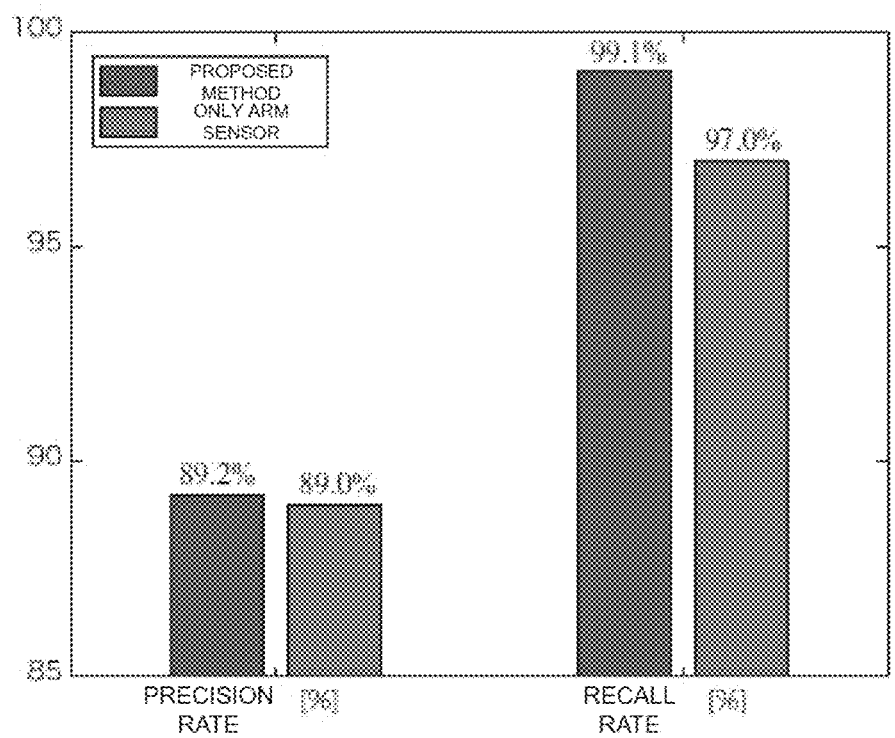
FIG. 6B is a diagram illustrating evaluation of a corrected estimated value.

The estimation accuracy of a proposed method and the estimation accuracy of a method only using the arm sensor 10 are compared using, among the obtained data sets, the data of eight persons under heating for one day in winter as test data and the other data as learning data. The test data includes, in addition to correct answer data of the thermal comfort level, which was reported at the same time as the acquisition of a thermal image every 30 minutes, the thermal comfort level reported at an arbitrary point in time. Comparison in the accuracy of the estimated value at the point in time when acquisition of a thermal image fails can be performed. FIG. 6A illustrates the precision rate and the recall rate of each method when the excess energy consumption state is expressed by (thermal comfort level) HC>0. The proposed method is superior to the method based on only the arm sensor 10 in terms of both the precision rate and the recall rate. In addition, the results indicate that when the proposed method is used, the recall rate is kept low whereas the precision rate is high, and air conditioning control that impairs the thermal comfort level of the user because of erroneous determination can be avoided. FIG. 6B illustrates the precision rate and the recall rate of each method when the excess energy consumption state is expressed by (thermal comfort level)*H⊇0. This indicates that the estimation of the excess energy consumption state ((thermal comfort level)*HC⊇0) is accurate in both methods. In a case where the neutral state is defined as having room for energy consumption reduction, the proposed method is indicated to work effectively. In addition, since the proposed method is slightly superior in terms of both the precision rate and the recall rate regardless of the definition of the excess energy consumption state, it was possible to confirm the effectiveness of using both the thermal image and the arm sensor 10.

(2) Second Embodiment

Figure 7:
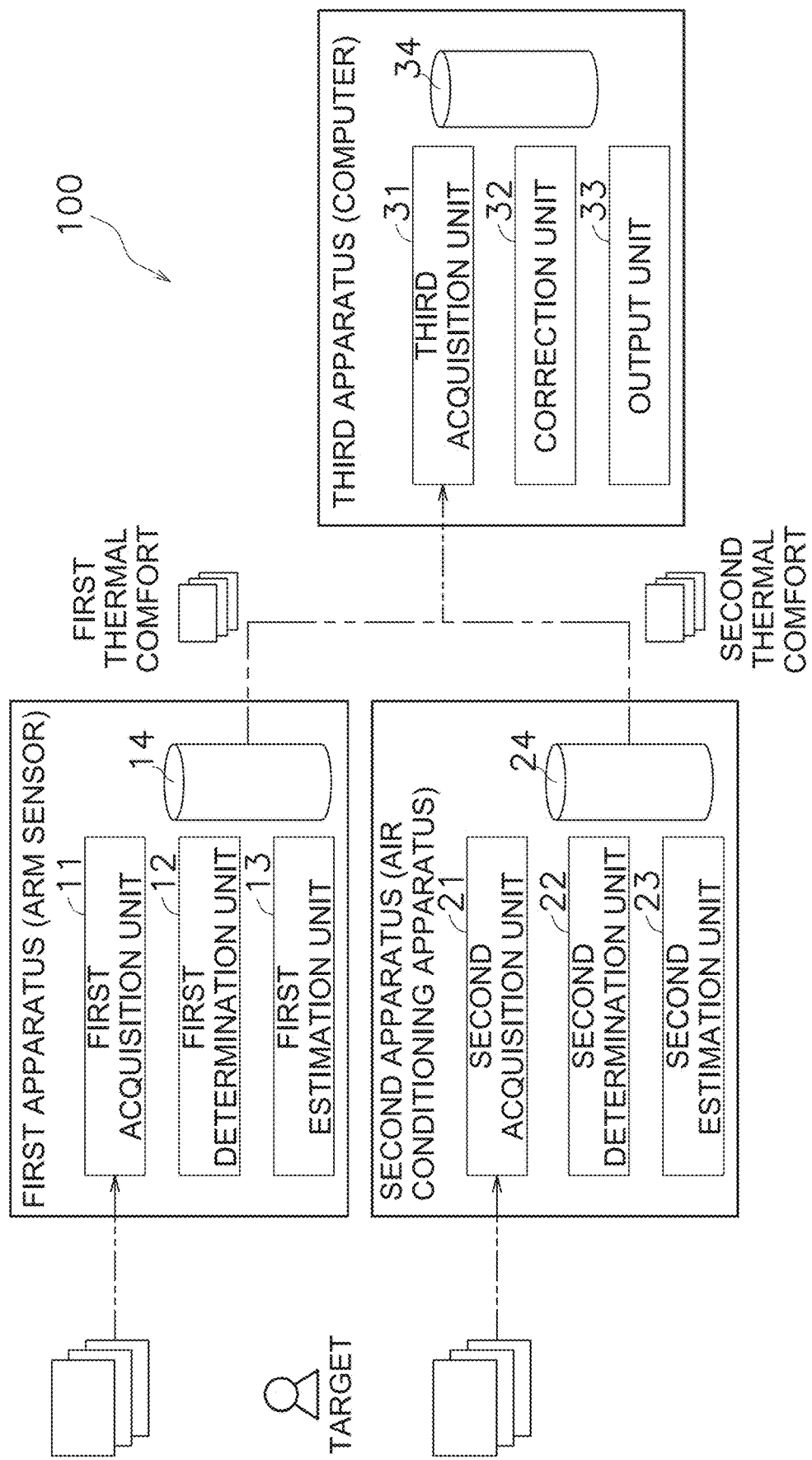
FIG. 7 is a schematic diagram of a system according to a second embodiment.

A second embodiment of a system 100 according to the present disclosure will be described with reference to FIG. 7. A description of a configuration and a calculation method similar to those of the first embodiment will be omitted.

(2-1) First Apparatus 10

A first apparatus 10 is, for example, an arm sensor presented in the first embodiment. The first apparatus 10 is capable of communicating with a second apparatus 20, a third apparatus 30, or any other apparatus via various networks. The first apparatus 10 includes a first acquisition unit 11, a first determination unit 12, a first estimation unit 13, and a first storage unit 14.

The first acquisition unit 11 includes one or more sensors and acquires first biological information while being in contact with a target living body. The first acquisition unit 11 includes, for example, sensors that acquire information on the target, such as a heart rate, a body surface temperature, and an electrodermal activity (EDA: Electro-Dermal Activity). The first acquisition unit 11 may acquire other information. The information acquired by the first acquisition unit 11 is stored in the first storage unit 14 as first biological information. In this embodiment, the first acquisition unit 11 is configured to acquire the first biological information at a time interval of once per minute. However, the first acquisition unit 11 presented in the present disclosure is not limited to this.

The first determination unit 12 determines whether the first biological information acquired by the first acquisition unit 11 is effective information. The first apparatus 10 has various parameters in advance, and the first determination unit 12 determines whether the first biological information is effective information on the basis of the various parameters. Alternatively, the first apparatus 10 compares the current first biological information acquired by the first acquisition unit 11 with the previous first biological information stored in the first storage unit 14 and determines whether the first biological information is effective information. The first storage unit 14 may store only the first biological information determined to be effective information by the first determination unit 12.

The first estimation unit 13 estimates a first thermal comfort of the target on the basis of the first biological information stored in the first storage unit 14. The first thermal comfort is estimated using, for example, a random forest. The first thermal comfort estimated by the first estimation unit 13 is stored in the first storage unit 14.

The first biological information and the first thermal comfort stored in the first storage unit 14 are stored in association with information on the time at which the first acquisition unit 11 acquired the first biological information. The first biological information and the first thermal comfort may be stored in association with each other.

(2-2) Second Apparatus 20

The second apparatus 20 is, for example, an air conditioning apparatus presented in the first embodiment. The second apparatus 20 is capable of communicating with the first apparatus 10, the third apparatus 30, or any other apparatus via various networks. The second apparatus 20 includes a second acquisition unit 21, a second determination unit 22, a second estimation unit 23, and a second storage unit 24.

The second acquisition unit 21 includes one or more sensors and acquires second biological information without coming into contact with the target living body. The second acquisition unit 21 includes, for example, sensors that acquire information such as the body surface temperature of the entire face, the body surface temperature of the forehead, the body surface temperature of the right cheek, the body surface temperature of the left cheek, the body surface temperature of the tip of the nose, and the body surface temperature around the mouth. The second acquisition unit 21 may acquire other information. The information acquired by the second acquisition unit 21 is stored in the second storage unit 24 as second biological information. In this embodiment, the second acquisition unit 21 intermittently acquires the second biological information.

The second determination unit 22 determines whether the second biological information acquired by the second acquisition unit 21 is effective information. The second apparatus 20 has various parameters in advance, and the second determination unit 22 determines whether the second biological information is effective information on the basis of the various parameters. Alternatively, the second apparatus 20 compares the current second biological information acquired by the second acquisition unit 21 with the previous second biological information stored in the second storage unit 24 and determines whether the second biological information is effective information. The second storage unit 24 may store only the second biological information determined to be effective by the second determination unit 22.

The second estimation unit 23 estimates a second thermal comfort of the target on the basis of the second biological information stored in the second storage unit 24. The second thermal comfort is estimated using, for example, a random forest. The second thermal comfort estimated by the second estimation unit 23 is stored in the second storage unit 24.

The second biological information and the second thermal comfort stored in the second storage unit 24 are stored in association with information on the time at which the second acquisition unit 21 acquired the second biological information. The second biological information and the second thermal comfort may be stored in association with each other.

(2-3) Third Apparatus 30

The third apparatus 30 is, for example, a computer. The third apparatus 30 is capable of communicating with the first apparatus 10, the second apparatus 20, or any other apparatus via various networks. The third apparatus 30 acquires the respective pieces of information from the first apparatus 10 and the second apparatus 20 at any time interval or in response to an operation of the target or the like and outputs a third thermal comfort. The third apparatus 30 includes a third acquisition unit 31, a correction unit 32, an output unit 33, and a third storage unit 34.

The third acquisition unit 31 acquires the first thermal comfort and the second thermal comfort from the first apparatus 10 and the second apparatus 20, respectively, via various networks. The third acquisition unit 31 stores the acquired first thermal comfort and second thermal comfort in the third storage unit 34. The first thermal comfort and the second thermal comfort may be acquired at different timings.

The correction unit 32 performs correction of the first thermal comfort on the basis of the second thermal comfort. Specifically, the correction unit 32 sets the weight of the second thermal comfort to be greater than the weight of the first thermal comfort, and calculates the third thermal comfort. The correction method is not limited to this. The correction unit 32 corrects the first thermal comfort on the basis of the second thermal comfort, which is a more accurate thermal comfort of the target. The third thermal comfort calculated through correction processing performed by the correction unit 32 is output from the output unit 33. Further, the third thermal comfort is stored in the third storage unit 34.

The output unit 33 outputs the third thermal comfort to the target or the like. For example, the output unit 33 outputs (displays) the third thermal comfort to a display of the third apparatus 30. Alternatively, the output unit 33 outputs (transmits) the third thermal comfort to the first apparatus 10 or the second apparatus 20.

(3) Features 3-1

The system 100 according to the present disclosure includes the first acquisition unit 11, the second acquisition unit 21, the first estimation unit 13, the second estimation unit 23, and the correction unit 32. The first acquisition unit 11 acquires first biological information while being in contact with a target living body. The first acquisition unit 11 includes one or more sensors. The second acquisition unit 21 acquires second biological information without coming into contact with the target living body. The second acquisition unit 21 includes one or more sensors different from the one or more sensors of the first acquisition unit 11. The first estimation unit 13 estimates a first thermal comfort of the target on the basis of the first biological information acquired by the first acquisition unit 11. The second estimation unit 23 estimates a second thermal comfort of the target on the basis of the second biological information acquired by the second acquisition unit 21. The second thermal comfort has higher accuracy than the first thermal comfort. The correction unit 32 corrects the first thermal comfort on the basis of the second thermal comfort.

Accordingly, the system 100 according to the present disclosure can acquire a more accurate thermal comfort of the target. While an arm sensor or the like serving as the first apparatus 10 is capable of constantly sensing biological information of the target, the first thermal comfort estimated by the first apparatus 10 may have low accuracy. While the second thermal comfort estimated by an air conditioning apparatus or the like serving as the second apparatus 20 has high accuracy, the air conditioning apparatus or the like is not capable of constantly sensing biological information of the target. In the system 100 according to the present disclosure, the first thermal comfort is corrected using the second thermal comfort having higher accuracy, thereby making it possible to acquire accurate thermal comfort in a shorter time interval than that of the second thermal comfort.

3-2

The system 100 according to the present disclosure includes the first acquisition unit 11, the second acquisition unit 21, and an estimation unit. The first acquisition unit 11 acquires first biological information of a target. The first acquisition unit 11 includes one or more sensors. The second acquisition unit 21 acquires second biological information of the target. The second acquisition unit 21 includes one or more sensors different from the one or more sensors of the first acquisition unit 11. The estimation unit estimates a thermal comfort of the target on the basis of the first biological information and the second biological information. The system learns using the first biological information, the second biological information, and the thermal comforts as teacher data. The system 100 receives the first biological information and the second biological information as input and outputs thermal comfort.

Accordingly, the system 100 according to the present disclosure can acquire a more accurate third thermal comfort than the first thermal comfort and the second thermal comfort.

3-3

The system 100 according to the present disclosure includes the first acquisition unit 11, the second acquisition unit 21, the first estimation unit 13, and the second estimation unit 23. The first acquisition unit 11 acquires first biological information of a target. The first acquisition unit 11 includes one or more sensors. The second acquisition unit 21 acquires second biological information of the target. The second acquisition unit 21 includes one or more sensors different from the one or more sensors of the first acquisition unit 11. The second estimation unit 23 estimates a second thermal comfort of the target on the basis of the first biological information acquired by the first acquisition unit 11 and the second biological information acquired by the second acquisition unit 21. The system 100 causes the first estimation unit 13 to learn using the first biological information acquired by the first acquisition unit 11 and an estimation result estimated by the second estimation unit 23 as a teacher data set. When the first estimation unit 13 performs estimation, the system 100 outputs the first thermal comfort on the basis of the first biological information acquired by the first acquisition unit 11.

3-4

The first acquisition unit 11 acquires, as the first biological information, at least information on any one of a heart rate, a body surface temperature, or an electrodermal activity (EDA: Electro-Dermal Activity) of the target. The second acquisition unit 21 acquires, as the second biological information, at least information on the body surface temperature of the face of the target and information on the body surface temperatures of the parts of the face. Further, the number of types of information included in the second biological information is larger than the number of types of information included in the first biological information.

The first apparatus 10 including the first acquisition unit 11 is, for example, an arm sensor. The arm sensor preferably includes sensors capable of acquiring information on a heart rate, a body surface temperature, and an electrodermal activity. The second apparatus 20 including the second acquisition unit 21 is, for example, an air conditioning apparatus. The air conditioning apparatus preferably includes a sensor such as a thermography and is capable of acquiring a thermal image. It is therefore possible to acquire information on the body surface temperature of the face of the target and information on the body surface temperatures of the parts of the face. The information on the body surface temperatures of the parts of the face includes information such as the body surface temperature of the entire face, the body surface temperature of the forehead, the body surface temperature of the right cheek, the body surface temperature of the left cheek, the body surface temperature of the tip of the nose, and the body surface temperature around the mouth.

3-5

The number of sensors included in the second acquisition unit 21 is preferably larger than the number of sensors included in the first acquisition unit 11. It is therefore possible to estimate a more accurate second thermal comfort. The concept of the number of sensors includes not only the number of physical sensors but also, if a plurality of pieces of information can be acquired based on data obtained by a single sensor, the meaning of the number of pieces of information.

3-6

The first apparatus 10 according to the present disclosure further includes the first determination unit 12. The first determination unit 12 determines whether the first biological information acquired by the first acquisition unit 11 is effective information. If the first determination unit 12 determines that the first biological information is effective, the first estimation unit 13 estimates a first thermal comfort.

The second apparatus 20 further includes the second determination unit 22. The second determination unit 22 determines whether the second biological information acquired by the second acquisition unit 21 is effective information. If the second determination unit 22 determines that the second biological information is effective, the second estimation unit 23 estimates a second thermal comfort.

Therefore, an error generated between the estimation result of the first thermal comfort obtained by the first apparatus 10 and the estimation result of the second thermal comfort obtained by the second apparatus 20 is reduced, resulting in an increase in the accuracy of the estimation of thermal comfort.

3-7

The first estimation unit 13 further estimates the first thermal comfort on the basis of the first biological information previously acquired by the first acquisition unit 11. The second estimation unit 23 further estimates the second thermal comfort on the basis of the second biological information previously acquired by the second acquisition unit 21.

Therefore, the first apparatus 10 or the second apparatus 20 can estimate the thermal comfort of the target on the basis of previously acquired biological information. The previously acquired biological information is stored in each storage unit.

(4) Modifications 4-1

The system 100 presented in the present disclosure may further include the third acquisition unit 31 that acquires information on a thermal environment surrounding the target. The third acquisition unit 31 acquires, as the information on the thermal environment surrounding the target, information on the ambient temperature and/or the ambient humidity of the living body. The third acquisition unit 31 may be disposed in the first apparatus 10, the second apparatus 20, the third apparatus 30, or any other apparatus.

The system 100 presented in the present disclosure can acquire a more accurate thermal comfort by estimating the thermal comfort of the target on the basis of a plurality of pieces of biological information. The air conditioning apparatus is controlled on the basis of this thermal comfort, thereby making it possible to perform more comfortable air conditioning.

4-2

The third apparatus 30 presented in the present disclosure acquires the first thermal comfort and the second thermal comfort from the first apparatus 10 and the second apparatus 20, respectively. However, the third apparatus 30 may acquire the first biological information and the second biological information from the first apparatus 10 and the second apparatus 20, respectively. The third apparatus 30 may include the functions of the first estimation unit 13 and the second estimation unit 23. The third apparatus 30 may acquire the third thermal comfort from the first biological information and the second biological information.

(5) Third Embodiment

In a third embodiment, as in the first embodiment, thermal comfort is estimated on the basis of a thermal image and biological data obtained by the arm sensor 10.

The estimation unit 13, 23, 32, which is constituted by the first estimation unit 13, the second estimation unit 23, and the correction unit 32, includes a learning device that performs machine learning. The learning device is capable of performing two types of learning during learning. The learning device may be constructed by one piece of hardware or a plurality of pieces of hardware.

In one learning in the estimation unit 13, 23, 32, learning is performed using, as teacher data, the body surface temperature of the face (second biological information), which is acquired from the thermal image, first biological information acquired from the arm sensor 10, and the thermal comfort reported by the test subject.

The other learning is learning performed when no thermal image can be obtained, and learning is performed by setting the body surface temperature of the face, which is obtained from the thermal image to $-300°$ C. (for example, a dummy value indicating that the body surface temperature is not included) and using, as teacher data, the first biological information obtained from the arm sensor 10 and the thermal comfort reported by the test subject.

In a case where a thermal image can be obtained in the estimation of thermal comfort, the estimation unit 13, 23, 32 receives the body surface temperature obtained from the thermal image and the first biological information obtained from the arm sensor 10 as input and estimate (output) thermal comfort. In a case where no thermal image can be obtained, in contrast, the estimation unit receives the body surface temperature as a dummy value (for example, $-300°$ C.) obtained from a thermal image and the first biological information obtained from the arm sensor 10 as input and estimate thermal comfort. Accordingly, even if the acquisition of the second biological information fails, it is possible to perform estimation.

However, the thermal comfort based on the dummy body surface temperature has a larger error than the thermal comfort with the presence of the body surface temperature, and, accordingly, there is a possibility that estimated values become large and discontinuous in response to switching based on whether the body surface temperature obtained from a thermal image is present. To address this, the thermal comfort based on the dummy body surface temperature is corrected on the basis of the difference between the thermal comfort with the presence of the body surface temperature and the thermal comfort based on the dummy body surface temperature, or correction is performed using a filter or the like that smooths changes using previous data of the thermal comfort with the presence of the body surface temperature and the thermal comfort based on the dummy body surface temperature. This can maintain continuity in response to switching.

(6) Features 6-1

The estimation unit 13, 23, 32 of the system 100 according to the third embodiment learns using the first biological information, the second biological information, and the thermal comfort as teacher data. The estimation unit 13, 23, 32 estimates the thermal comfort on the basis of the first biological information and the second biological information. The estimation unit 13, 23, 32 stores the estimated thermal comfort of the target. Further, the estimation unit 13, 23, 32 has a function of outputting dummy information when the second acquisition unit does not acquire the second biological information. The estimation unit 13, 23, 32 learns using the first biological information, the dummy information, and the thermal comfort as teacher data. The estimation unit 13, 23, 32 sets, as the thermal comfort of the target, the first thermal comfort that is corrected on the basis of the first biological information, the dummy information, and the stored thermal comfort.

6-2

The estimation unit of the system 100 according to the third embodiment learns using the first biological information, the second biological information, and the thermal comfort as teacher data. The estimation unit 13, 23, 32 estimates the thermal comfort on the basis of the first biological information and the second biological information. The estimation unit 13, 23, 32 stores the estimated thermal comfort of the target. Further, the estimation unit 13, 23, 32 has a function of outputting dummy information when the second acquisition unit does not acquire the second biological information. The estimation unit 13, 23, 32 learns using the first biological information, the dummy information, and the thermal comfort as teacher data. The estimation unit 13, 23, 32 learns using the first biological information, the dummy information, and the stored thermal comfort as teacher data, and sets, as the thermal comfort of the target, the first thermal comfort that is estimated on the basis of the first biological information and the dummy information.

7

While embodiments of the present disclosure have been described, it will be understood that forms and details can be changed in various ways without departing from the spirit and scope of the present disclosure as recited in the claims.

What is claimed is:

1. A system comprising:
a first acquisition unit configured to acquire first biological information of a target, the first acquisition unit including at least one first sensor;
a second acquisition unit configured to acquire second biological information of the target, the second acquisition unit including at least one second sensor different from the at least one first sensor of the first acquisition unit; and
an estimation unit configured to estimate a thermal comfort of the target based on the first biological information and the second biological information,
the estimation unit being further configured to estimate
a first thermal comfort of the target based on the first biological information, and
the thermal comfort of the target based on the first biological information and the second biological information, and
when the second acquisition unit does not acquire the second biological information, the estimation unit is further configured to set, as the thermal comfort of the target, the first thermal comfort that is corrected using previous thermal comfort of the target estimated by the estimation unit based on at least the second biological information previously acquired by the second acquisition unit.

2. A system comprising:
a first acquisition unit configured to acquire first biological information of a target, the first acquisition unit including at least one first sensor;
a second acquisition unit configured to acquire second biological information of the target, the second acquisition unit including at least one second sensor different from the at least one first sensor of the first acquisition unit;
a first estimation unit configured to estimate a first thermal comfort of the target based on the first biological information;
a second estimation unit configured to estimate a thermal comfort of the target based on the first biological information and the second biological information; and
a correction unit configured to correct the first thermal comfort, when the second acquisition unit does not acquire the second biological information, using previous thermal comfort of the target estimated by the second estimation unit based on the at least the second biological information previously acquired by the second acquisition unit.

3. A system comprising:
a first acquisition unit configured to acquire first biological information of a target, the first acquisition unit including at least one first sensor;
a second acquisition unit configured to acquire second biological information of the target, the second acquisition unit including at least one second sensor different from the at least one first sensor of the first acquisition unit;
a first estimation unit configured to estimate a first thermal comfort of the target based on the first biological information acquired by the first acquisition unit; and
a second estimation unit configured to estimate a second thermal comfort of the target based on the second biological information acquired by the second acquisition unit,
the first estimation unit being configured to learn a relationship between the first biological information acquired by the first acquisition unit and an estimation result estimated by the second estimation unit to estimate the estimation result estimated by the second estimation unit from the first biological information acquired by the first acquisition unit using a teacher data set that associates the first biological information acquired by the first acquisition unit with the estimation result estimated by the second estimation unit, and when the first estimation unit performs estimation, the first thermal comfort based on the first biological information acquired by the first acquisition unit being output.

4. The system according to claim 1, wherein the first acquisition unit is configured to acquire the first biological information while being in contact with the target, and the second acquisition unit is configured to acquire the second biological information without coming into contact with the target.

5. The system according to claim 1, wherein the first acquisition unit is configured to acquire, as the first biological information, at least information on any one of a heart rate, a body surface temperature, or an electrodermal activity of the target.

6. The system according to claim 1, wherein the second acquisition unit is configured to acquire, as the second biological information, at least information on a body surface temperature of a face of the target and information on a body surface temperature of a part of the face.

7. The system according to claim 1, wherein a number of types of information included in the second biological information is larger than a number of types of information included in the first biological information.

8. The system according to claim 3, wherein the second thermal comfort has higher accuracy than the first thermal comfort.

9. The system according to claim 1, wherein a number of the at least one second sensor included in the second acquisition unit is larger than a number of the at least one first sensor included in the first acquisition unit.

10. The system according to claim 3, further comprising:

a second determination unit configured to determine whether the second biological information acquired by the second acquisition unit is effective information on the basis of various parameters obtained in advance, the second estimation unit being configured to estimate the second thermal comfort in a case in which the second determination unit determines that the second biological information is effective.

11. The system according to claim 3, further comprising:

a first determination unit configured to determine whether the first biological information acquired by the first acquisition unit is effective information on the basis of various parameters obtained in advance, the first estimation unit being configured to estimate the first thermal comfort in a case in which the first determination unit determines that the first biological information is effective.

12. The system according to claim 3, wherein the first estimation unit is further configured to estimate the first thermal comfort based on the first biological information previously acquired by the first acquisition unit, or the second estimation unit is further configured to estimate the second thermal comfort based on the second biological information previously acquired by the second acquisition unit.

13. The system according to claim 1, further comprising:

a third acquisition unit configured to acquire information on a thermal environment surrounding the target.

14. The system according to claim 13, wherein the third acquisition unit is configured to acquire information on one or both of an ambient temperature and an ambient humidity of the target.

15. The system according to claim 1, wherein the estimation unit is further configured to learn a relationship between the first biological information, the second biological information, and the thermal comfort of the target to estimate the thermal comfort of the target from the first biological information and the second biological information using teacher data that associates the first biological information, the second biological information, and the thermal comfort of the target, when the second biological information is not acquired, the estimation unit is configured to learn a relationship between the first biological information, dummy information distinguishable from the second biological information, and the thermal comfort of the target to estimate the thermal comfort of the target from the first biological information and the dummy information distinguishable from the second biological information using teacher data that associates the first biological information, the dummy information distinguishable from the second biological information, and the thermal comfort of the target, when the first biological information and the second biological information are acquired, the estimation unit is configured to estimate the thermal comfort of the target and to store an estimated value of the thermal comfort of the target, and when the second biological information is not acquired, the estimation unit is configured to estimate the first thermal comfort based on the first biological information and the dummy information, and to set, as the thermal comfort of the target, the first thermal comfort that is corrected based on stored previous the thermal comfort of the target.

16. The system according to claim 15, wherein when learning a relationship between the first biological information, the dummy information, and the thermal comfort of the target to estimate the thermal comfort of the target from the first biological information and the dummy information using teacher data that associates the first biological information, the dummy information, and the thermal comfort of the target, the estimation unit is configured to use the stored estimated value of the thermal comfort of the target as the thermal comfort of the target, and when the second biological information is not acquired, the estimation unit is configured to set, as the thermal comfort of the target, the first thermal comfort that is corrected by learning.

* * * * *